(12) United States Patent
Gauss et al.

(10) Patent No.: US 6,991,714 B1
(45) Date of Patent: Jan. 31, 2006

(54) APPARATUS AND METHOD FOR TAKING SAMPLES FROM POLYMER SUPPORT MATERIAL

(75) Inventors: Christine Gauss, Geretsried (DE); Martin Horn, Berlin (DE); Markus Kalkum, Berlin (DE); Holger Eickhoff, Berlin (DE)

(73) Assignee: Max-Planck-Gesellschaft zur Foederung der Wissenschaften e.V., Munich (DE)

( * ) Notice: Subject to any disclaimer, the term of this patent is extended or adjusted under 35 U.S.C. 154(b) by 0 days.

(21) Appl. No.: 09/647,910

(22) PCT Filed: Mar. 26, 1999

(86) PCT No.: PCT/EP99/02059

§ 371 (c)(1),
(2), (4) Date: Dec. 7, 2000

(87) PCT Pub. No.: WO99/51977

PCT Pub. Date: Oct. 14, 1999

(30) Foreign Application Priority Data

Apr. 6, 1998 (DE) .................................. 198 15 400

(51) Int. Cl.
- *G01N 27/26* (2006.01)
- *G01N 1/00* (2006.01)
- *B01L 3/00* (2006.01)

(52) U.S. Cl. ...................... 204/462; 204/456; 204/613; 204/606; 422/99; 422/101; 73/863; 73/863.31

(58) Field of Classification Search ................ 204/613, 204/456–470, 606–621; 422/99–101, 63–67; 436/514–516; 435/287.3; 73/863, 863.31–32
See application file for complete search history.

(56) References Cited

U.S. PATENT DOCUMENTS

| | | | |
|---|---|---|---|
| 4,341,735 A | 7/1982 | Seifried | |
| 4,653,369 A | 3/1987 | Dunsirn | |
| 5,144,872 A * | 9/1992 | Kakimoto | ...................... 83/13 |
| 5,146,794 A | 9/1992 | Rising et al. | |
| 5,306,510 A * | 4/1994 | Meltzer | ...................... 422/65 |
| 5,587,062 A | 12/1996 | Togawa et al. | |
| 5,993,627 A * | 11/1999 | Anderson et al. | ........... 204/456 |

FOREIGN PATENT DOCUMENTS

| | | |
|---|---|---|
| DE | DD50356 | 9/1966 |
| DE | DD83659 | 8/1971 |
| DE | 3043419 | 10/1982 |
| DE | G921252 | 2/1993 |
| DE | 19628178 | 9/1997 |
| EP | 539888 | 5/1993 |
| EP | 577084 | 1/1994 |
| EP | 810438 | 12/1997 |
| GB | 2067126 | 7/1981 |
| JP | 6273291 | 9/1994 |

(Continued)

*Primary Examiner*—Nam Nguyen
*Assistant Examiner*—Jeffrey Barton
(74) *Attorney, Agent, or Firm*—Robert A. Koons, Jr.; Matthew P. McWilliams; Drinker, Biddle & Reath

(57) ABSTRACT

A sample taking apparatus comprises a plurality of separation tools (10) (for example, punching capillaries) on a holding device (20), wherein the separation tools (10) are each provided with actuating means (30) for separate control thereof. In a sample taking method (for example, for punching samples from separation gels), successively removed samples are deposited in parallel onto a target substrate.

15 Claims, 2 Drawing Sheets

FOREIGN PATENT DOCUMENTS

Figure 1:
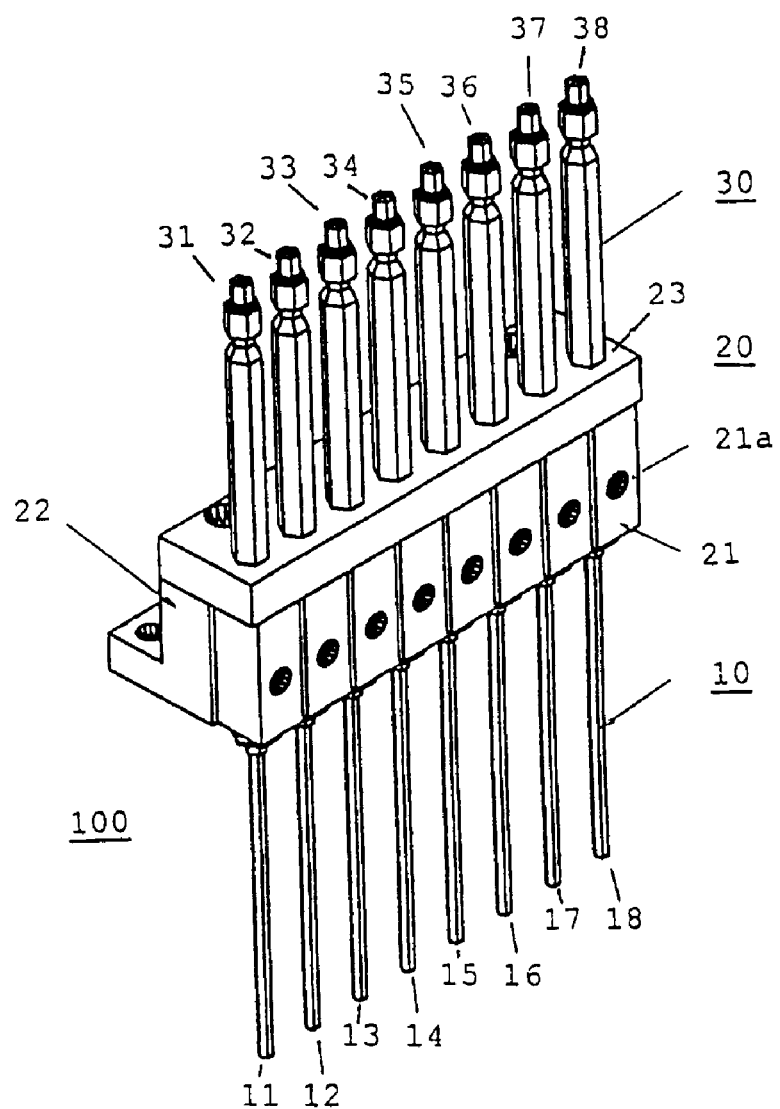

| | | |
|---|---|---|
| JP | 6273292 | 9/1994 |
| WO | 9011876 | 10/1990 |
| WO | 9408234 | 4/1994 |
| WO | 9713838 | 4/1994 |
| WO | 9523960 | 9/1995 |
| WO | 9930168 | 6/1999 |

* cited by examiner

APPARATUS AND METHOD FOR TAKING SAMPLES FROM POLYMER SUPPORT MATERIAL

This application is a National Stage entry of International Application No. PCT/EP99/02059, filed Mar. 26, 1999, and claims benefit of foreign priority to German Application No. 198 15 400.3, filed Apr. 6, 1998.

The invention relates to a sample taking apparatus which is configured to receive or transfer a plurality of samples from polymer support materials, and a method for use of such a sample taking apparatus. The invention relates, in particular, to taking samples by separating partial areas with certain substances from the support materials, such as, for example, punching of substance bands from separation gels.

From chemistry, biology, medicine, and molecular biotechnology numerous separation methods are known in general in which substance mixtures in a support medium are substance-specifically spatially separated and, subsequently, are subjected to further processing steps. In the field of genome research, for the separation of, for example, protein mixtures, genome sequences or DNS mixtures, electrophoretic separation methods with one or more dimensional separation gels are used.

In the two-dimensional gel electrophoresis, for example, proteins are separated according to their acid or base characteristic in a first dimension by means of a first separation step and in a second dimension as a function of size by means of a second separation step. As a result, the separated fragments are located in a so-called two-dimensional gel which has the form of a gel layer of a surface area of approximately 8 cm×12 cm to 20 cm×30 cm and a thickness of approximately 0.5 mm to 1 mm. After separation, the fragments are dyed for the purpose of visualization with organic (conventional dyes such as, for example, Coomassie blue, fluorescent dyes) or inorganic (for example, silver staining) substances so that bands, blots, or irregularly shaped spots are formed. In the following, the separated fragments in a support medium are generally referred to as bands. The bands are irregularly distributed in the two-dimensional gel depending on the substance properties. For further processing or analysis of the separated fragments, the bands in the past have been cut out manually or semi-automatically by means of a scalpel from the gel in order to then perform specific further examinations, for example, by mass spectrometry.

In the aforementioned applications in genome research but also, for example, in the modern combinatorial chemistry, there is an interest to separate in time periods as short as possible a number of substances as large as possible and to further process the separated fragments or samples. The separation technique as well as the further analytical examination of the samples nowadays provide for a high sample throughput. The transfer of separated fragments onto substrates, which represent the starting point for further processing, however, represents a bottleneck to this day.

It is an object of the invention to provide an apparatus and a method for taking samples, which are improved so as to allow a greater number of samples being simultaneously processed. The invention is particularly directed to applications in the gel electrophoretic separation methods.

This object is solved by an apparatus and a method including the features according to claims 1 and 10, respectively. Preferred embodiments of the invention are apparent from the dependent claims.

The basic idea of the invention resides in the provision of a sample taking device with a plurality of individually actuatable separation tools which are commonly movable in a reference plane at a spacing from the material from which samples are to be taken, and are selectively movable or actuatable toward the material. The sample separation from the material is carried out preferably serially. This means that the sample taking device is moved always alternating to a certain position in the reference plane, and then one of the separation tools for sample loading is actuated. For movement in the reference plane the sample taking device is provided with an adjusting device. The sample transfer onto a target substrate can then be carried out simultaneously and parallel from all separation tools.

The control of the sample taking device is carried out preferably in combination with an image taking system. The image taking system comprises a camera device with which the sample positions (for example, band positions) are detected. Based on the sample positions, the target coordinates for each movement of the adjusting device are derived. The combination of a sample taking device (with a plurality of separation tools) with an image taking device is an important feature of the invention because this makes possible an automated operation and acceleration of the entire sample taking process.

The invention is generally usable in all processes in which samples are to be taken from a support or sample material and transferred onto a target substrate. The term sample taking therefore in general refers to the separation (for example, cutting, punching, stamping or the like) of the sample from the material and the placement of the separated sample in a predetermined way on a target substrate. The invention can be carried out especially beneficially with polymer support materials (layer-shaped or volume-shaped) or with other materials (for example, membranes or biological materials such as cell clusters arranged on substrates). The target substrate is preferably a microtiter plate. A preferred application of the invention resides in the controlled removal of samples from separation gels, wherein the removal positions are determined by image processing in a predetermined way and wherein the advancing to the removal positions and the sample removal by means of the separation tools (punching capillaries) are carried out sequentially, and in the transfer of the taken samples into the depressions of a microtiter plate, wherein a temporally parallel sample deposition in the depressions is provided for the transfer.

Figure 2:
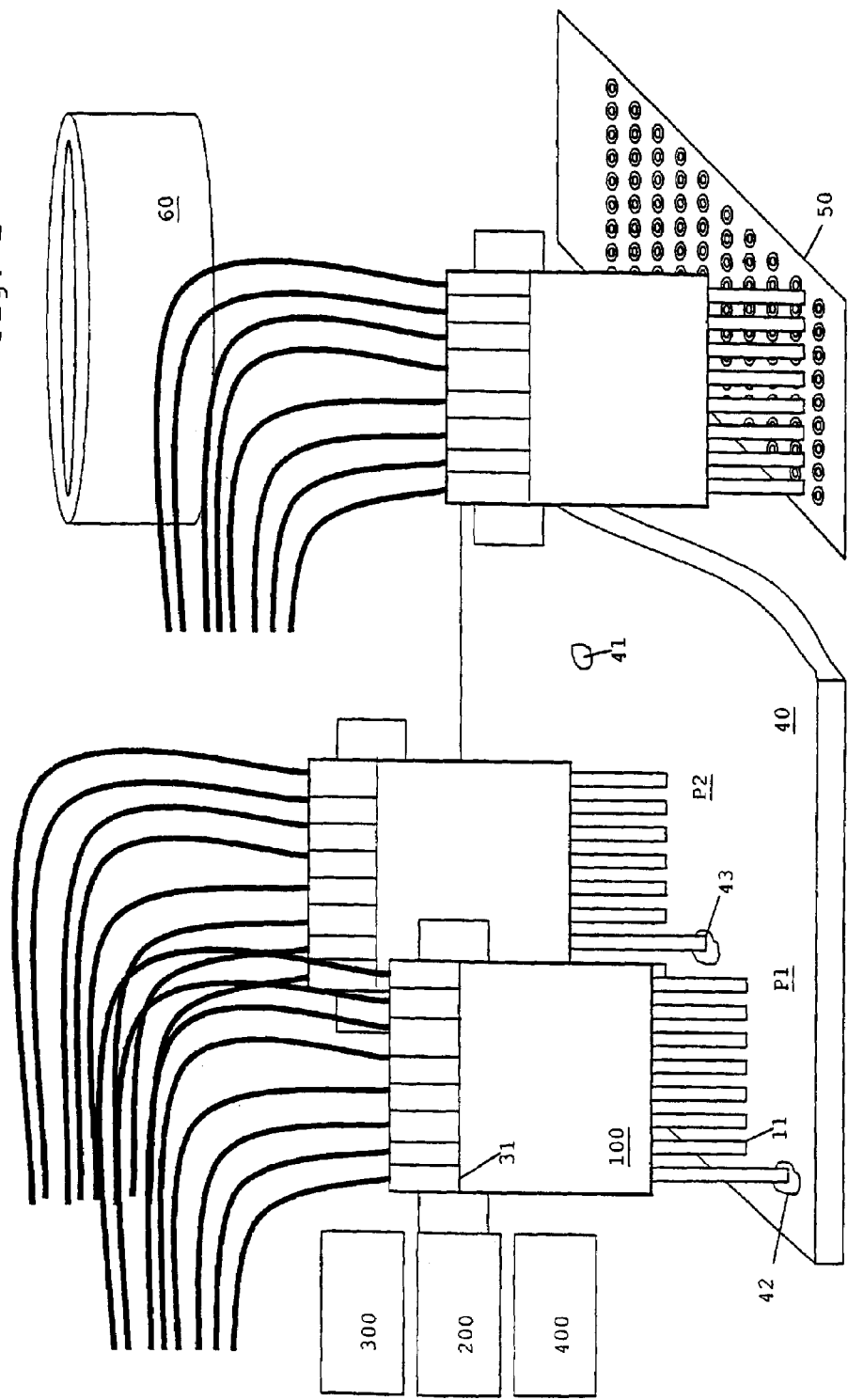

Further details and advantages of the invention are described in the following with reference to the Figures, showing:

FIG. 1 a perspective view of a sample taking device according to the invention; and FIG. 2 a schematic overview representation for illustrating the method according to the invention.

The invention will be described in the following with reference to a sample taking apparatus with a row of separation tools which comprise eight capillary-shaped punching tools. The invention, however, is not limited to this embodiment but can be implemented with separation tools shaped differently, with separation tools arranged like a matrix with rows and columns, or with separation tools whose number changes depending on the application.

The sample taking apparatus 100 according to the invention comprises according to FIG. 1 a plurality of separation tools 10, a holding device 20, and a plurality of actuating means 30.

The separation tools 10 comprise tubular punching or stamping tools, for example, in the form of punching capillaries 11 through 18. As an alternative, other cutting tools can be provided also. Each punching tool is connected at one end with a guide portion 21 of the holding device 20 so as to be moveable in the axial direction. At the other end of each punching tool a cutting edge is provided. The cross-sectional shape, the geometric dimensions, and the relative arrangement of the punching tools are determined based on the application. For sample taking on separation gels, each punching tool is preferably formed by a capillary at whose end the cutting edge is provided by the end of the capillary wall. The inner diameter of the capillary is selected based on the application and is preferably less than the thickness of the material (separation gel, membranes or the like) from which the sample is to be taken. For conventional two-dimensional separation gels, the inner diameter is preferably approximately 0.5 to 2 mm, for example, approximately 1 mm. The thickness and the material of the capillary wall are selected in order to provide a sufficient durability for the separation step. The capillaries can be comprised of an inert material such as, for example, metal, glass, ceramic or plastic material. Steel capillaries are preferred because of their high durability. The relative spacing between the capillaries is adjusted depending on the application based on the conditions of the target substrates. When the target substrates is, for example, a microtiter plate (see FIG. 2), the capillary spacing corresponds to the reservoir spacing of the microtiter plate (for example. 9 mm).

The holding device 20 is comprised of guide parts 21, a connecting plate 22 and a holding plate 23. The connecting plate 22 is provided with an adjusting device (not shown) for connecting the holding device 20. The adjusting device is configured for movement of the sample taking device into a reference plane to certain target coordinates, as will be explained infra. The holding plate 23 serves as a common holder for the guide parts 21 and the actuating means 30 and for the connecting plate 22.

For each separation tool (for example, for each capillary) a guide part 21 is provided which has a double function. Firstly, by means of the guide part 21 an axial movability of the separation tools from a basic position into a punching position is determined. Moreover, each guide part 21 contains a connecting opening 21a via which the respective separation tool can be loaded by pressure, or alternatively vacuum, by means of a pressure system (not represented). The vacuum serves to secure the punched-out sample in the separation tool. When it is desired to place the samples onto the target substrate, the vacuum is replaced with a slight overpressure (in any case, for example, approximately ½ technical atmosphere). The connecting opening 21a can moreover be used for supplying a rinsing liquid.

For preventing sample migration in the capillary, a retaining device can be provided inside thereof which separates a sample volume at the end of the capillary from the remainder of the capillary and which can be formed, for example, by a pin in the capillary.

The actuating means 30 comprise a group of pneumatic cylinders 31, 32, . . . , 38 each associated to a respective separation tool. The pneumatic cylinders are operated by compressed air and include electrical switching valves, respectively. When a certain pneumatic cylinder is activated by actuation of the electrical switching valve, the corresponding separation tool is moved in the axial direction by an advancing stroke. After completion of the punching process, the separation tool is returned due to the action of an internal spring element or an external restoring spring or equally by pressure application. An important advantage of the invention is that the separation tools or punching tools can be individually controlled so that the sample taking can be adjusted to any type of sample format.

Instead of the pneumatic cylinders, the actuating means 30 can comprise other drive elements, for example, hydraulic (with hydraulic cylinder), piezoelectric or electromagnetic drives.

The holding device 20 is connected to the adjusting device such that the direction of axial movement of the cutting tools is substantially perpendicularly to the (movement) reference plane of the adjusting device.

A sample taking method is explained in the following with reference to FIG. 2. FIG. 2 shows schematically the sample taking device 100 in different method phases as well as the adjusting device 200, an imager 300, and a control device 400 in an example of taking a sample from a separation gel 40. Essentially known arrangements based on so-called "spotting and picking" robots can be used as the adjusting and control devices. The control device 400 sends to the adjusting device 200 respective target coordinates to which the sample taking device 100 is to be moved. The target coordinates are obtained as follows by means of the imager 300. As a separation gel 40 a two-dimensional gel on a planar substrate is illustrated as an example. As an alternative, the invention can also be implemented correspondingly with a one-dimensional gel, for example, in a layer or band shape.

The image taking device 300 comprises a camera (not shown) for obtaining a digital image of the two-dimensional gel 40 with the regularly or irregularly arranged dyed bands 41. The camera is preferably connected, like the sample taking device, with the adjusting device and is movable above the two-dimensional gel in the reference plane (x-y plane) parallel to the plane of the gel 40. The digital image is processed in the control device 400. The image evaluation advantageously is not necessarily referring to defined markings on the separation gel substrate but to the separate bands or spots in the separation gel. With the invention it was possible to demonstrate for the first time that these bands or spots, which have a variable contrast relative to the surroundings, are also suitable for image taking and evaluation. For larger size bands or spots it is even possible to provide several punching steps (for example, spot diameter 2 mm, punching capillary diameter approximately 1 mm: 2 to 3 punching steps per spot). In the control device a program sequence is provided which, as a function of the size of the band, determines the target coordinates and determines how often adjacent gel pieces are to be taken from a band. The target coordinates refer to the position of the sample taking device 100 relative to a band in the two-dimensional gel while considering the relative coordinates of the punching capillary respectively to be selected. An important aspect of the invention is that, after image taking and processing or evaluation, a desired one of the samples is automatically taken in a time sequence with the punching capillaries from the separation gel. Advantageously, the entire image recognition can be carried out automatically. An operator-controlled camera control is not a compulsory requirement. According to the separation result, the punching positions are irregular based on the application and are not distributed according to a predetermined pattern. By using the imager 300, which serves as an optical positioning device, a target-oriented punching is possible even for irregular band or spot distribution.

By means of the adjusting device 200, the sample taking apparatus is arranged such that the spacing of the punching capillaries, in its basic position, from the substrate on which the gel is located corresponds substantially to the advancing distance of the actuating means (see supra).

After taking the digital image and determining the target coordinates, the sample taking device 100 is first moved into the first position P1 in which one of the punching capillaries (for example, 11) is aligned relative to a certain band 42 in the separation gel. As soon as the position P1 has been reached, the pneumatic cylinder 31 is actuated so that the punching capillary 11 is shot into the gel and the sample is received at the capillary end. Subsequently, the adjusting device 200 moves the sample taking device 100 to the next position P2 where the same process is repeated with the next punching capillary (for example, 12). The position P2 can relate to a different sample in the same band 42 or in another band 43. In this way, the positions P1 to P8 are approached according to the number of punching capillaries (P3 to P8 are not shown). The punching capillaries are therefore sequentially loaded at the positions P1 to P8. The sequentially loaded punching capillaries must not necessarily be loaded in the sequence of their arrangement.

Subsequently, when all or some punching capillaries, depending on the application, are loaded, the sample taking device is moved to the target substrate, for example, in the form of a microtiter plate 50. The sample taking device 100 is positioned such that the ends of the punching capillaries are positioned opposite the respective reservoirs of the microtiter plate 50. The individual samples are deposited in the reservoirs by application of pressure to the punching capillaries. The deposition of the samples on the microtiter plate 50 is carried out across all punching capillaries simultaneously, i.e. parallel. The deposition of the samples is advantageously sample-specific. This means that each individual sample or group of samples corresponding to a common band is deposited separately in individual reservoirs. The samples are transferred into an ordered grid for further assay or analysis. Subsequently, optionally with interposition of a cleaning step in a cleaning bath 60, the next sequence of sample taking on the sample substrate 40 is carried out.

The sequential sample taking with the punching capillaries and the parallel sample deposition are repeated as many times as it takes to punch out all bands on the separation gel.

The system illustrated in FIGS. 1 and 2 can be modified in that not a straight row of separation tools but a curved row or a matrix arrangement of separation tools is provided. Moreover, it can be arranged such that during the sample taking sequence several sample pieces are taken up in sequence by a punching capillary. It is even possible with a correspondingly matched sample deposition that in one punching capillary several samples of different bands are received. In the case of multi-loading of the punching capillaries, it can be provided that between the samples separation pieces, for example, from a gel area without sample, are taken. Finally, it is possible that at one position (P1, P2. . . . .) optionally several punching capillaries can be actuated simultaneously.

The sample taking system according to the invention has the advantage that punching speeds on the separation gels of approximately 1000 samples per hour can be reached. This greatly surpasses conventional punching speeds with manual or semi-automatic punching devices of approximately 200 samples per hour. The sample taking can be automated. The high punching speed has the additional advantage that the punching of, for example, a two-dimensional separation gel with more than 1000 proteins can be finished before the separation gel possibly has changed geometrically as a function of time and thus would exclude a further reproducible processing.

What is claimed is:

1. A sample taking apparatus, arranged for receiving a plurality of samples from a separation gel, comprising a plurality of separation tools (10) for taking samples of the separation gel, wherein the separation tools (10) are arranged on a holding device (20), and are provided with respective actuating means (30), by which the separation tools (10) can be separately controlled and moved.

2. The sample taking apparatus according to claim 1, wherein the separation tools are tubular punching tools (11 to 18) which at one end thereof are axially movably arranged on the respective actuating means (31 to 38) and have, at the other end thereof, a punching edge.

3. The sample taking apparatus according to claim 2, wherein the punching tools (11 to 18) are formed as capillaries.

4. The sample taking apparatus according to claim 1, wherein the actuating means (30) are selected from the group consisting of pneumatic cylinders, hydraulic cylinders, piezoelectric actuating devices, and electromagnetic actuating devices.

5. The sample taking apparatus according to claim 1, wherein the separation tools (10) are arranged on the holding device (20) in a matrix having at least one row.

6. The sample taking apparatus according to claim 5, wherein the separation tools (10) are arranged such that their ends form an array which corresponds to the array of sample reservoirs in a predetermined microtiter plate format.

7. The sample taking apparatus according to claim 1, wherein each separation tool (10) is connected by a guide means (21) to the respective actuating means (30), wherein each guide means (21) has a connecting opening (21a) whereby the separation tool is connected to a pressure system.

8. The sample taking apparatus according to claim 1, wherein the holding device (20) is connected to an adjusting device (200) for positioning the holding device (20) with the separation tools (10) in a horizontal or x-y reference plane.

9. The sample taking device according to claim 8, further comprising an imager (300) and a control device (400), wherein the imager (300) supplies image data of a separation gel to the control device, which is arranged to generate target coordinates for controlling the adjusting device (200).

10. A method for cutting samples from a separation gel and transferring said samples onto a target substrate (50), said method comprising:
cutting said samples from a separation gel successively in time using a sample taking apparatus (100) having a plurality of separation tools (10), that are separately controlled and moved; and transferring said samples onto said target substrate (50) simultaneously in parallel.

11. The method according to claim 10, wherein alternatingly first the sample taking apparatus (100) is moved by an adjusting device (200) into a position (P1, P2, . . . ) corresponding to predetermined target coordinates and then one or more separation tools (31 to 38) are actuated until all or some separation tools (31 to 38) are loaded with removed samples, whereupon the sample taking device (100) is moved to the target substrate (50) and the samples are transferred from the separation tools onto the target substrate (50).

12. The method according to claim 11, wherein the target coordinates of the positions (P1, P2, . . . ) are obtained from image data of the separation gel.

13. The method according claim 10, wherein the separation tools (30) are actuated by compressed air or a hydraulic liquid.

14. The method according to claim 10, wherein the samples are substance bands (41, 42, 43) distributed in the separation gel, and the target substrate is a microtiter plate (50).

15. The method according to claim 10, further comprising the steps of
applying an underpressure to the separation tools containing removed samples prior to the transfer; and
applying an overpressure to the separation tools containing removed samples to effect the transfer onto the target substrate.

* * * * *